US012629447B2

(12) United States Patent
Lai et al.

(10) Patent No.: US 12,629,447 B2
(45) Date of Patent: May 19, 2026

(54) SHAPE MEMORY MATERIAL WITH CHELATING SYSTEM AND PREPARATION METHOD THEREOF

(71) Applicant: SHENZHEN INSTITUTES OF ADVANCED TECHNOLOGY, Shenzhen (CN)

(72) Inventors: Yuxiao Lai, Shenzhen (CN); Yuanchi Zhang, Shenzhen (CN); Wei Zhang, Shenzhen (CN)

(73) Assignee: SHENZHEN INSTITUTES OF ADVANCED TECHNOLOGY, Shenzhen (CN)

( * ) Notice: Subject to any disclaimer, the term of this patent is extended or adjusted under 35 U.S.C. 154(b) by 517 days.

(21) Appl. No.: 18/044,655

(22) PCT Filed: Nov. 24, 2022

(86) PCT No.: PCT/CN2022/133923
§ 371 (c)(1),
(2) Date: Mar. 9, 2023

(87) PCT Pub. No.: WO2024/108469
PCT Pub. Date: May 30, 2024

(65) Prior Publication Data
US 2024/0293598 A1      Sep. 5, 2024

(51) Int. Cl.
*A61L 27/04*      (2006.01)
*A61L 27/18*      (2006.01)
(52) U.S. Cl.
CPC ............. *A61L 27/047* (2013.01); *A61L 27/18* (2013.01); *A61L 2430/02* (2013.01)
(58) Field of Classification Search
CPC .... A61L 27/047; A61L 27/18; A61L 2430/02; A61L 27/04; A61B 17/11; A61F 2/28
See application file for complete search history.

(56) References Cited

U.S. PATENT DOCUMENTS

2005/0228103 A1 10/2005 Bringley et al.
2022/0204806 A1* 6/2022 Vercaemst ............. C08G 69/42

FOREIGN PATENT DOCUMENTS

CN       102921038 A      2/2013
CN       109078228 A      12/2018
(Continued)

OTHER PUBLICATIONS

Vincenzo Guarino, et al. Bioactive scaffolds for bone and ligament tissue, Expert review of medical devices, 4.3 (2007): 405-418.
(Continued)

*Primary Examiner* — Yashita Sharma
(74) *Attorney, Agent, or Firm* — D'Ambrosio & Menon, PLLC; Usha Menon

(57) ABSTRACT

The present invention provides a shape memory material with a chelating system. The shape memory material with the chelating system comprises polyurethane and a metal complex in a mass ratio of 100:(1-10), and the polyurethane is obtained by reaction of the following components by weight percent: 9.0-10.0% of methylenediphenyl diisocyanate, 0-2.0% of chain extender, 0-3.0% of chelating agent, and 87.0-88.0% of polycaprolactone diol. The present invention provides a novel shape memory material polyurethane-manganese dioxide (SMPU-MnO$_2$) chelating material. Collaboration of its mechanical strength, shape memory performance and Mn$^{2+}$ responsive release is achieved through the chelating system, and shape recovery is performed by means of the photothermal effect of manganese dioxide under remote control of near-infrared light to achieve self-fixed filling of an irregular bone defect part and responsively release manganese ions, so as to achieve a bone repair biological function.

8 Claims, 4 Drawing Sheets

(56) References Cited

FOREIGN PATENT DOCUMENTS

| | | | |
|---|---|---|---|
| CN | 109337087 A | 2/2019 | |
| CN | 109880054 A | 6/2019 | |
| CN | 113214450 A | 8/2021 | |
| CN | 114533660 A | 5/2022 | |
| CN | 114618014 A | 6/2022 | |
| GB | 886186 A | 1/1962 | |
| WO | WO-2007084725 A2 * | 7/2007 | ............. A61L 27/58 |

OTHER PUBLICATIONS

Ruiqi Xie, et al. Self-fitting shape memory polymer foam inducing bone regeneration: A rabbit femoral defect study, Biochimica et Biophysica Acta (BBA)-General Subjects 1862.4 (2018): 936-945.
International Searching Authority. International Search Report and Written Opinion for PCT Application No. PCT/CN2022/133923 and English translation, mailed Aug. 7, 2023 pp. 1-15.
Yuanchi Zhang et al. "3D-printed NIR-responsive shape memory polyurethane/magnesium scaffolds with tight-contact for robust bone regeneration" Bioactive Materials, vol. 16, Dec. 31, 2021 (Dec. 31, 2021), pp. 218-231 ISSN: 2452- 199X.

* cited by examiner

SHAPE MEMORY MATERIAL WITH CHELATING SYSTEM AND PREPARATION METHOD THEREOF

CROSS-REFERENCE TO RELATED APPLICATION

This application is a national stage filing under 35 U.S.C. § 371 of international application number PCT/CN2022/133923, filed Nov. 24, 2022. The contents of the international application are incorporated herein by reference in its entirety.

TECHNICAL FIELD

The present invention belongs to the technical field of bone tissue repair, and particularly relates to a shape memory material with a chelating material and a preparation method thereof.

BACKGROUND

Repair of large-range bone defects caused by fractures and trauma has always been one of the most concerned problems in the field of public health. To overcome the limitation of autogenous bone graft, bone tissue engineering materials have been increasingly developed in recent years. As a kind of stimuli-responsive smart materials, shape memory polymers (SMPs) have been used for research on bone defect repair. Besides implementation of minimally invasive surgery and biocompatibility, the shape memory polymers further can realize the self-fixing function of tightly filling irregular defect sites, so as to enhance the interaction between the materials and tissue interfaces. In addition, in order to meet the requirement of repairing biological environment, SMPs are usually compounded with inorganic nanoparticles to improve the mechanical strength and the biological activity of the materials. Shape memory polyurethane (SMPU) is one of classic SMPs and can be endowed with a specific temporary shape and fixed under certain external conditions. Suffered from external stimulation such as heat, light, electricity or water, the SMPU will respond and recover the initial shape from the temporary shape, to finish a cycle of shape memory and even memorize a plurality of states and reversible deformations. The SMPU further features light weight, better recovery performance, mild recovery condition, better biocompatibility, low price and the like, so it has been developed rapidly in recent years. The SMPU usually consists of two parts: a molecular chain network structure and a switch. The molecular chain network structure is usually formed by crosslinking molecular chains of a polymer, which decides the recovery performance and the initial shape of the SMPU. The switch is formed by a reversible switch of semi-crystalline structure-melting transition, glass transition of an amorphous region or a chemical bond, which decides the fixity of the temporary shape of the SMPU. With respect to different application demands, different functional or stimuli-responsive modes can be designed smoothly by selecting specific components. Researchers at home and abroad have reported application of the shape memory material in many fields, including aerospace, textile and garment, artificial intelligence, biomedicines and the like. Intelligent medical materials/devices reported presently include degradable self-shrinkable surgical sutures, artificial muscles, self-expanded memory heart scaffolds, vascular scaffolds and the like. In the field of bone repair, a scaffold prepared based on the shape memory material can be compressed to a smaller size before being implanted, and recovers the shape in the defect site after being implanted and is tightly attached to the irregular defect site to achieve a self-fixing function, so as to enhance the interactions between the enhancing materials and the tissue interfaces such as concentrations of active ingredients and photothermal effect, thereby better inhibiting in-situ relapse or metastasis of tumors and promoting bone tissue regeneration in the defect site.

In order to meet the requirements on bone repair, the SMPU needs to be further modified to improve its mechanical performance and the biological function. A conventional solution is to prepare shape memory composite materials (SMCs) by adding inorganic particle fillers, so as to endow it with biological activity and improve the mechanical strength. Manganese dioxide ($MnO_2$) has huge research value and clinical application potential. For example, $MnO_2$ can release manganese ions ($Mn^{2+}$) under an acidic condition and under the action of glutathione in a microenvironment of bone tumor tissues, and $Mn^{2+}$ has excellent performance in activating the immune system to inhibit tumors. Moreover, $MnO_2$ is also used for preparing a composite material to achieve a purpose of promoting bone regeneration. However, after the inorganic filler is added, the SMCs may still have some limitations to restrict its clinical application, including difficulty to precisely regulate and control release of active ions. Release of biological active ions plays an important role of realizing effectiveness of biological function of the SMCs. However, at present, there are still short of researches in release behavior of the active ions of the SMCs in the bone repair environment and its biological effect in researches at home and abroad. Further, in 2007, Guarino, Vincenzo et. al have mentioned in published articles that the mechanical performance of the shape memory bone repair material can be improved by adding inorganic nanoparticles, but its shape memory performance is reduced somewhat (Expertreviewofmedicaldevices, 4.3 (2007): 405-418). In 2018, Ruiqi Xie et al. have improved the previous solution and prepared a shape memory polyurethane (SMPU)/hydroxyapatite (HA) composite scaffold by taking water as a foaming agent (BiochimicaetBiophysicaActa(BBA)-GeneralSubjects 1862.4(2018):936-945). However, the synthetic route used thereby is relatively complicated, and the prepared porous scaffold is poor in uniformity of pore diameter. The Chinese patent application CN102921038A discloses a method for preparing a porous scaffold with a shape memory function. In this method, the porous scaffold is prepared by taking benzoyl peroxide as a crosslinking initiator, allyl alcohol as a plasticizer and polycaprolactone diol as a base material. But polycaprolactone diol has certain flaws: its melting point is about 60° C., its heat resistance and the machining property are poor, and its shape memory performance is only 20%. Also, the response temperature needed by deformation of the SMCs may exceed a body temperature while the mechanical strength is improved, so the SMCs cannot recover its shape in vivo. Therefore, at present, the SMCs for bone repair faces the problems that the release of the active ions is difficult to be precisely regulated and controlled, and the mechanical strength, the shape memory performance and the response temperature are hardly collaborated.

SUMMARY

In order to solve the problems in the prior art that the release of active ions is difficult to precisely regulate and control, and mechanical strength, shape memory performance and response temperature are hardly collaborated for shape memory composite materials (SMCs) for bone repair, the present invention provides a shape memory material with a chelating system.

The shape memory material with the chelating system comprises polyurethane and a metal complex in a mass ratio of 100:1, wherein polyurethane is obtained by reaction of the following components by weight percent:

9.0-10.0% of methylenediphenyl diisocyanate, 0-2.0% of chain extender, 0-3.0% of chelating agent, and 87.0-88.0% of polycaprolactone diol.

Further, the mass ratio of methylenediphenyl diisocyanate, the chain extender, the chelating agent and polycaprolactone diol is 11.1:1:15.4:100.

Further, the quantity ratio of hydroxyl group contained in the chain extender, the chelating agent and polycaprolactone diol to isocyanate group contained in methylenediphenyl diisocyanate is (1.0-1.2):1.

Further, the metal complex is manganese dioxide with a particle size of 20-100 nm, and the mass ratio of manganese dioxide to polyurethane is (2-10):100, preferably 10:100.

Further, the chelating agent is pyridinedimethanol, N,N-bis(2-hydroxyethyl)isonicotinamide or 2,2-dimethylol propionic acid.

Further, the chain extender is 1,4-butanediol, 1,6-hexanediol or glycol.

Further, a number average molecular weight of polycaprolactone diol is 3000-8000.

An objective of the present invention is to provide a method for preparing a shape memory material with a chelating system.

The method for preparing the shape memory material with the chelating system comprises the following steps:

S1: mixing dried polycaprolactone diol with methylenediphenyl diisocyanate to react at 85° C., wherein a stirring speed is 150 rmp/min, and a stirring time is 2-3 h;

S2: dispersing a chain extender and a chelating agent in a solvent, and dropwise adding the obtained mixture in a prepolymer formed in S1, and continuing to react to be cured to obtain polyurethane; and S3: weighing polyurethane and the metal complex in a mass ratio of 100:10, dissolving the weighed polyurethane in an organic solvent, and then adding the metal complex to react, and curing to obtain the shape memory material with the chelating system.

The present invention provides a novel shape memory polyurethane-manganese dioxide (SMPU-MnO$_2$) chelating material. Collaboration of its mechanical strength, shape memory performance and Mn$^{2+}$ responsive release is achieved through a chelating system, and shape recovery is performed by means of the photothermal effect of manganese dioxide under remote control of near-infrared light to achieve self-fixed filling of an irregular bone defect part and responsively release manganese ions, so as to achieve a bone repair biological function.

DETAILED DESCRIPTION

Figure 1:
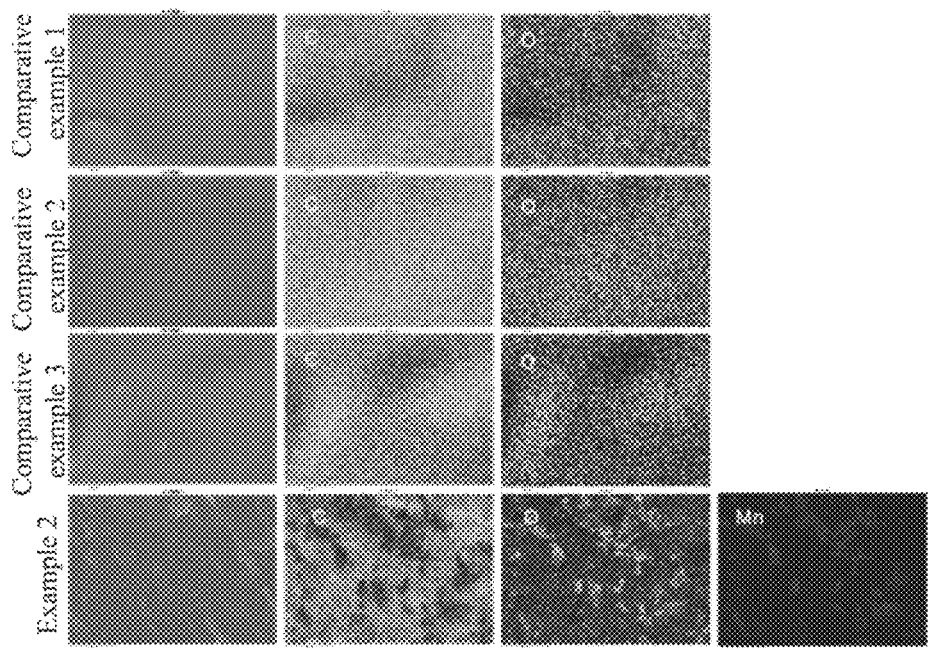
FIG. 1 is a surface topography and element distribution diagram.

To make the objectives, features and advantages of the present invention more obvious and understandable, the specific embodiments of the present invention will be described in detail in combination with drawings, but these embodiments cannot be construed as limitation to the implementable range of the present invention.

To solve the problems existed in the shape memory composite materials (SMCs) for bone repair that the release of the active ions is difficult to be precisely regulated and controlled, and the mechanical strength, the shape memory performance and the response temperature are hardly collaborated, the present invention is to provide a shape memory material with a chelating system, which can responsively release the active ions and collaborate multiple performance of the material, so as to improve the machinability, the mechanical performance, the ossification promoting performance and the shape memory performance. Moreover, the manufacturing method of the material is relatively simple, is liable to industrial implementation and has wide applicability.

In the present patent application, specified description on molecular weight of a polycaprolactone diol material defines the average molecular weight of the raw material rather than the molecular weight of each polymer molecule.

In raw materials in methods for preparing SMPU/MnO$_2$ chelating materials provided in comparative examples and examples, the molecular weight of the polycaprolactone diol (PLC-diol) is 5000. The used chain extender is 1,4-butanediol (BDO), and the used chelating agent is pyridinedimethanol (PDM). Optionally, PDM can be replaced by a small molecule compound containing both bis/trihydroxyl and pyridine nitrogen/carboxyl such as N,N-bis(2-hydroxyethyl) isonicotinamide and 2,2-dimethylolpropionic acid. PCL-diol is a soft segment of the SMPU, and BDO, PDM and methylenediphenyl diisocyanate (MDI) form the hard segment of the SMPU. In the SMPU/MnO$_2$ chelating material, the mass fraction of MnO$_2$ (relative to SMPU) is 10% in the example. Optionally, manganese dioxide can be replaced by other metals and oxides thereof capable of forming active metal coordinate bonds. Raw materials and amounts thereof used in the comparative examples 1-4 and the examples 1-2 are shown in the following table:

| | sample number | PCL-diol (g) | MDI (g) | BDO (g) | PDM (g) | MnO$_2$ (g) |
|---|---|---|---|---|---|---|
| Comparative example 1 | BS | 22.5 | 2.5 | 0.45 | 0 | 0 |
| Comparative example 2 | PS | 22.5 | 2.5 | 0 | 0.695 | 0 |
| Comparative example 3 | BPS | 22.5 | 2.5 | 0.5 | 0.5 | 0 |
| Comparative example 4 | BS-Mn | 22.5 | 2.5 | 0.45 | 0 | 2.5 |
| Example 1 | PS-Mn | 22.5 | 2.5 | 0 | 0.695 | 2.6 |
| Example 2 | BPS-Mn | 22.5 | 2.5 | 0.5 | 0.5 | 2.6 |

A method for preparing SMPU in comparative examples and examples comprises the following steps:

1. drying PCL-diol, MDI and BDO in a vacuum drying oven in a vacuum environment at 105° C. for 2 h to thoroughly remove moisture;
2. mixing and stirring PCL-diol and MDI in a proportion after drying, wherein the reaction temperature is kept at 85° C., the stirring speed is 150 rmp/min, and the stirring time is 2-3 h;
3. stirring BDO and PDM in a certain proportion in 10 mL of tetrahydrofuran to be dispersed for 1 h, ultrasonically dispersing the mixture for 1 h, and then dropwise adding the mixed solution into a prepolymer solution, continuing to stir and react, wherein the stirring time is 5-10 min; and
4. rapidly pouring the mixture into a polytetrafluoroethylene die after stirring, putting the polytetrafluoroethylene die into an oven to cure the mixture for 16 h at the temperature of 85° C. to obtain an SMPU solid.

A method for preparing a $MnO_2$-containing material in Comparative example 4 and Examples 1-2 comprises the following steps:

1. stirring the prepared SMPU in an organic solvent to be dissolved;
2. adding $MnO_2$ (a mass ratio of SMPU to $MnO_2$ is 100:10) after SMPU is fully dissolved, and fully stirring and evenly mixing the mixture; and
3. rapidly pouring the mixture into a polytetrafluoroethylene die after stirring, putting the polytetrafluoroethylene die in an oven to cure the mixture for 16 h at the temperature of 85° C. to obtain the SPMU solid.

Compared with the prior art, the present invention has the following advantages.

1. Aiming at the characteristics of bone repair, particularly problems of large area, irregularity and liability to relapse of refractory bone defects after osteosarcoma surgery, the present invention provides a shape memory polyurethane-manganese dioxide chelating material, which achieves a self-fixing function of tightly filling irregular defect sites, thereby enhancing the interaction between the material and the tissue interface.
2. The chelating material provided by the present invention can have the shape memory function, improves the mechanical strength of the material, and meanwhile responsively releases the active metal ions, promotes regeneration effectively, and is more suitable for a true bone repair environment.
3. Most of the conventional shape memory devices utilize a body temperature response function, which limits the mechanical performance and the response environment of the material. In the present invention, near-infrared light is used to activate the photothermal effect of the material so as to regulate and control the in vivo response process, which prevents the shape recovery of the conventional thermal response polyurethane from being limited by a body temperature.

In the present invention, the prepared material is used in the technical field of bone tissue repair materials, which can solve the problems that the release of the active ions and the mechanical strength is difficult to be precisely regulated and controlled, the shape memory performance and the response temperature are hardly collaborated. For example, in bone defects, the material can recover shape to enhance the interfacial interaction between the material and the tissue. In addition, in the bone defect caused by bone tumor surgery, the material can responsively release manganese ions according to the microenvironment of tumor to repair the defect while activating its own immune system, thereby achieving multiple functions.

The surface topography and element distribution in Comparative examples 1-3 and Example 2 are shown in FIG. 1. In examples, the Mn element can be seen clearly.

Figure 2:
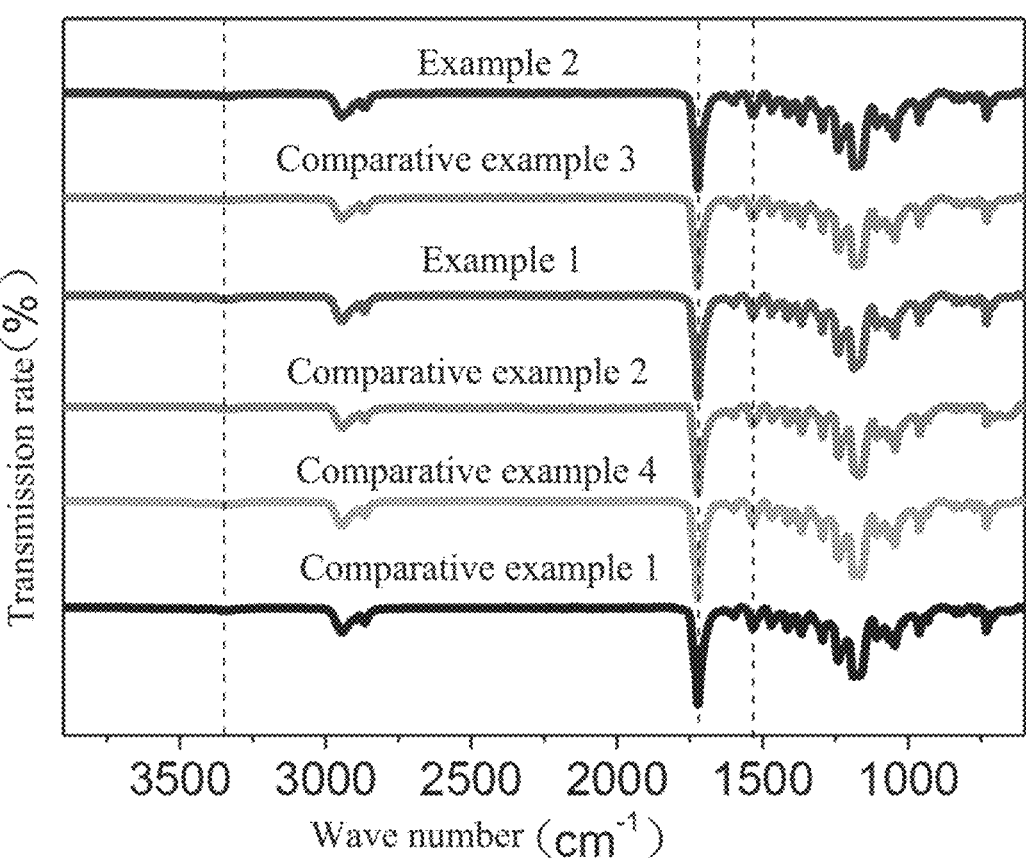
FIG. 2 is an infrared spectrogram.

Comparison of infrared spectra in Comparative examples 1-4 and Examples-2 are shown in FIG. 2. In the infrared spectra, it can be seen that urethane groups are present in SMPU.

Figure 3:
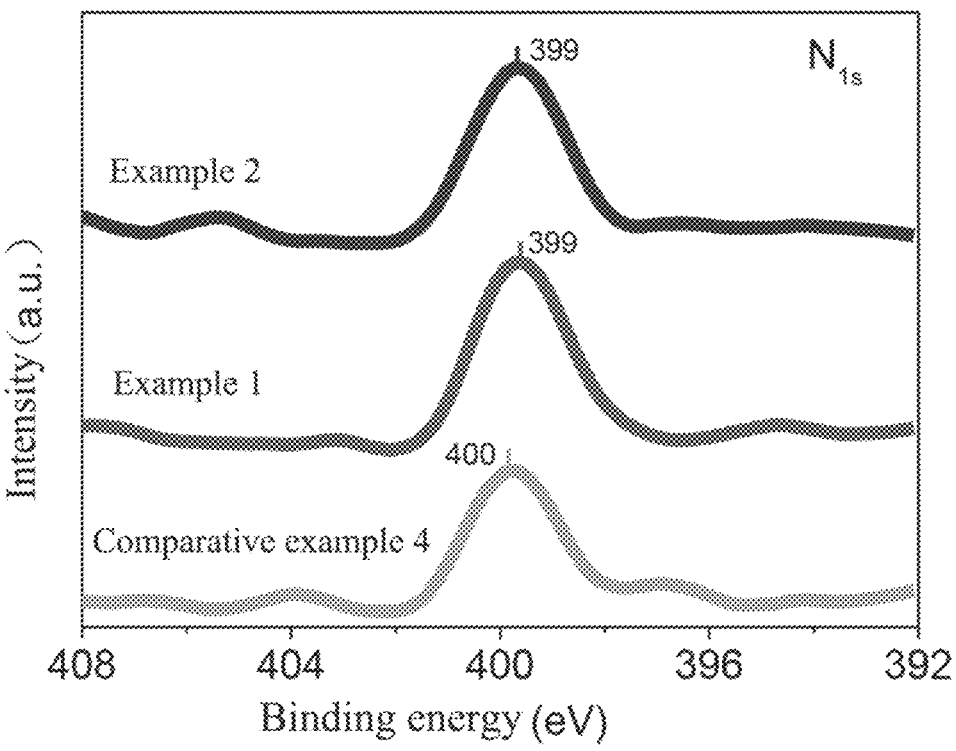
FIG. 3 is an XPSN1$_s$ spectrogram.

Comparison on $XPSN_{1s}$ spectra in Examples 1-2 is shown in FIG. 3. In Comparative example 4, the binding energy position of $N_{1s}$ is at 400 ev; whereas, in Examples 1 and 2, due to the presence of chelating bonds, the bonding energy position of $N_{1s}$ shifts and is located at 399 ev.

Figure 4:
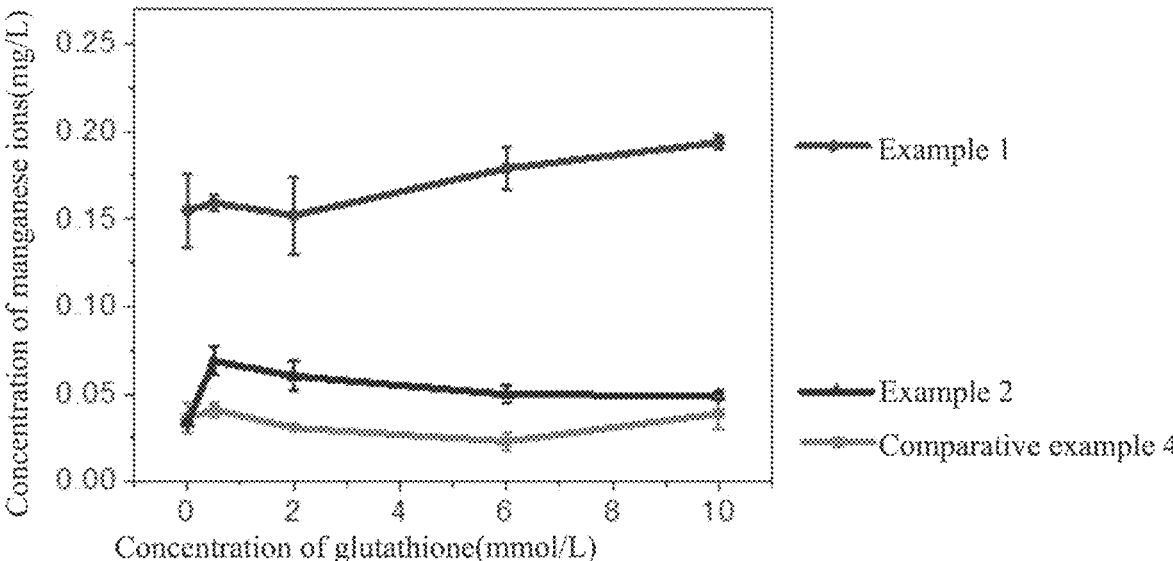
FIG. 4 shows a release concentration of manganese ions.

Comparison on release concentrations of manganese ions under different glutathione concentrations in Examples 2-4 and Comparative example 4 is shown in FIG. 4. In Comparative example 4, no chelating agent is added, so the prepared sample is free of the chelating system. In Examples 1 and 2, chelating agents are all added, so the prepared sample contains the chelating system. The amounts of manganese added in Examples 1 and 2 and Comparative example 4 are close. In the glutathione environment, the concentrations of the manganese ions released in the samples prepared in Examples 1 and 2 are all higher than that of the manganese ions released in the sample prepared in Comparative example 1. The concentration of the active manganese ions released in example with the chelating system is higher than that of the active manganese ions released in comparative example without the chelating system, illustrating that the chelating system in the shape memory composite material for bone repair provided by the present invention is capable of improving the release capacity of the manganese ions and the capacity of promoting bone regeneration. Therefore, the shape memory composite material is suitable for bone tissue repair.

Figure 5:
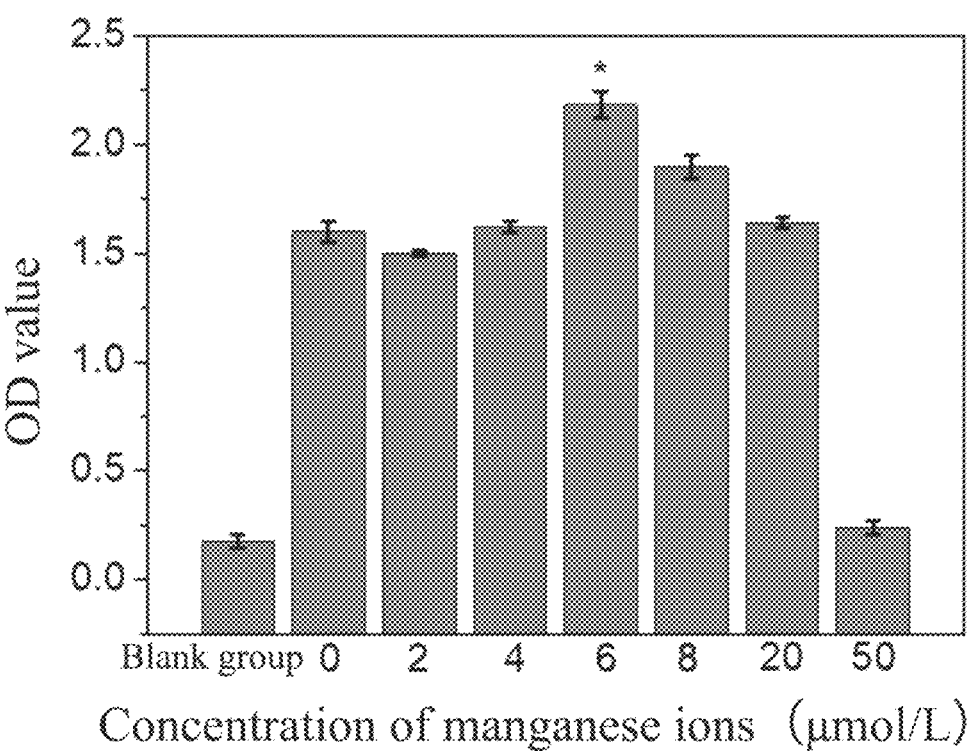
FIG. 5 shows osteogenic differentiation promoting effects at different concentrations of manganese ions.

FIG. 5 provides quantitative analytical data of alizarin red dyeing under different concentrations of manganese ions. It can be seen that when the concentration of the manganese ions is 6 μmol/L, the highest data can be obtained, i.e., the optimum osteogenic differentiation promoting effect. This verifies that different concentration of manganese ions have different osteogenic differentiation promoting effects to cells, so the chelating system regulates and controls release of manganese ions to better promote bone regeneration. It can be seen according to difference and ingredient table of the concentrations of the manganese ions released in the samples in Examples 1 and 2 in FIG. 4 that, by slightly increasing the amount of manganese, the release concentration of the manganese ions can be obviously improved. In FIG. 4, the release concentration of the manganese ions in the sample prepared in Example 1 in the glutathione environment can reach up to 0.2 mg/L, i.e., 3.6 μmol/L. On this basis, the release concentration of the sample in the bone defect position can be improved to 6 μmol/L by adjusting the amount of manganese added into the sample, so as to obtain the optimum osteogenic differentiation promoting effect.

Figure 6A:
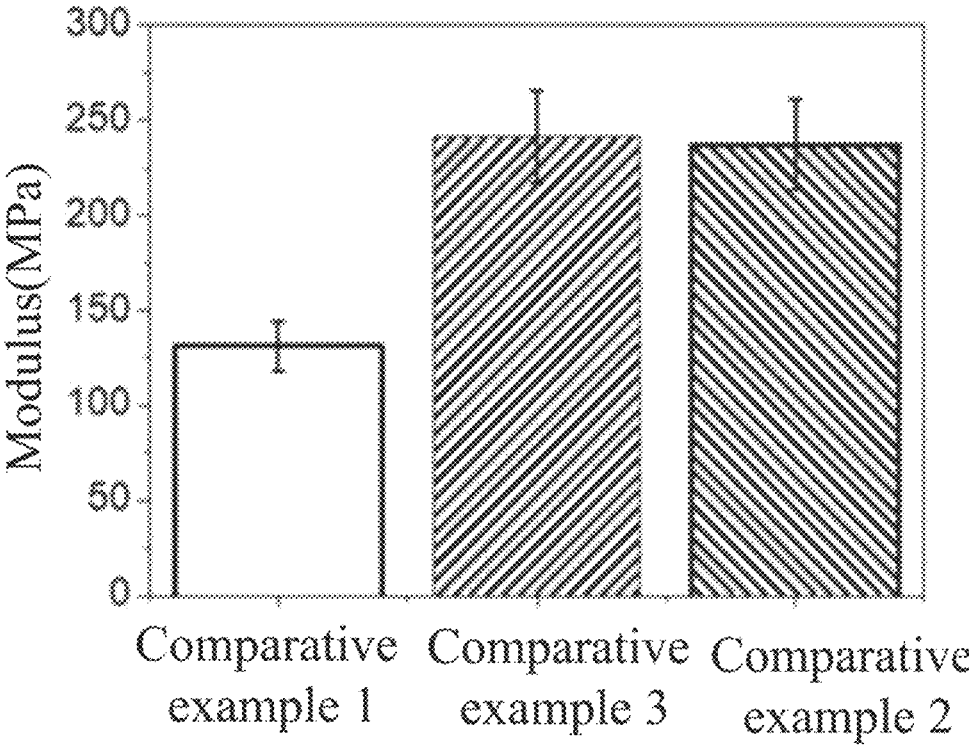
FIG. 6a is modulus comparison of a comparative example in a film state.

Comparison on tensile modulus (film state) in Comparative examples 1-3 and Example 2 is shown in FIG. 6a. The tensile modulus of the material is improved to some extent after the chelating agent is added. The material in Comparative example 3 with the highest modulus and the material compounded with manganese dioxide in Example 2 are further manufactured to obtain porous scaffolds, with comparison on the maximum compressive force shown in FIG. 6b. It can be seen from FIG. 6b that the compressive force of the porous scaffold prepared from the sample with the chelating system compounded with manganese ions prepared in Example 2 is higher than that of the porous scaffold prepared from the sample with the chelating system not compounded with manganese ions prepared in Comparative example 3, illustrating that the strength of the sample material is further improved by the chelating system with manganese dioxide in the sample.

Figures 6B, 7:
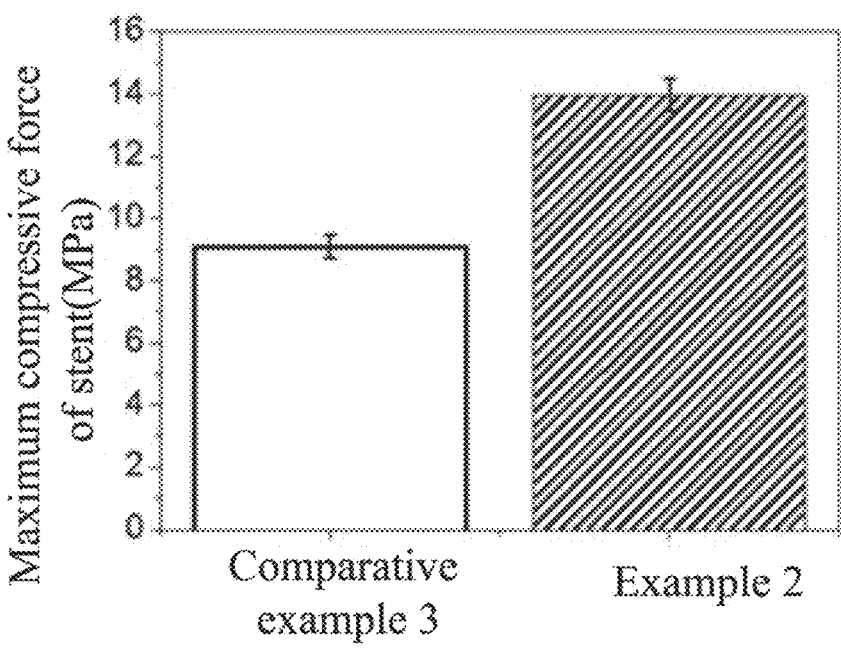
FIG. 6b is maximum compressive force comparison of a prepared bone repair device (a porous scaffold).
FIG. 7 shows photothermal effect and shape memory effect.

The photothermal effect and the shape memory effect of Example 1 are shown in FIG. 7, illustrating that the sample prepared in Example 1 under irradiation of near-infrared light at 120 seconds can be recovered to the original shape. The wavelength of the near-infrared light is 808 nm, and the power density is 1 w/cm$^2$.

The above experimental results show that there is a chelating structure compounded with manganese ions in the shape memory material with the chelating system provided by the present invention. In the presence of the chelating structure, not only can the release concentration of manganese ions be regulated and controlled to promote bone regeneration, but also the mechanical strength of the material is enhanced. In addition, the material can further respond to light and heat to achieve self-recovery of shape. Thus, it can be seen that the shape memory material with the chelating system provided by the present invention solves the problems that the release of the active ions of the current bone repair material is difficult to be precisely regulated and controlled, and the mechanical strength, the shape memory performance and the response temperature are hardly collaborated, thereby achieving multiple functions of the bone repair material.

The invention claimed is:

1. A shape memory material with a chelating system, comprising polyurethane and a metal complex in a mass ratio of 100:(1-10), wherein polyurethane is obtained by reaction of the following components by weight percent:
    9.0-10.0% of methylenediphenyl diisocyanate,
    0-2.0% of chain extender,
    0-3.0% of chelating agent, and
    87.0-88.0% of polycaprolactone diol.

2. The shape memory material with the chelating system according to claim 1, wherein the mass ratio of methylenediphenyl diisocyanate, the chain extender, the chelating agent and polycaprolactone diol is 11.1:1:15.4:100.1:15.4:100.

3. The shape memory material with the chelating system according to claim 1, wherein the quantity ratio of hydroxyl group contained in the chain extender, the chelating agent and polycaprolactone diol to isocyanate group contained in methylenediphenyl diisocyanate is (1.0-1.2):1.

4. The shape memory material with the chelating system according to claim 1, wherein the metal complex is manganese dioxide with a particle size of 20-100 nm, and the mass ratio of manganese dioxide to polyurethane is (2-10):100.

5. The shape memory material with the chelating system according to claim 1, wherein the chelating agent is pyridinedimethanol, N,N-bis(2-hydroxyethyl) isonicotinamide or 2,2-dimethylol propionic acid.

6. The shape memory material with the chelating system according to claim 1, wherein the chain extender is 1,4-butanediol, 1,6-hexanediol or glycol.

7. The shape memory material with the chelating system according to claim 1, wherein a number average molecular weight of polycaprolactone diol is 3000-8000.

8. A method for preparing a shape memory material with a chelating system, comprising the following steps:
    S1: mixing dried polycaprolactone diol with methylenediphenyl diisocyanate to react at 85° C., wherein a stirring speed is 150 rmp/min, and a stirring time is 2-3 h;
    S2: dispersing a chain extender and a chelating agent in a solvent, and dropwise adding the obtained mixture in a prepolymer formed in S1, and continuing to react to be cured to obtain polyurethane; and
    S3: weighing polyurethane and the metal complex in a mass ratio of 100:10, dissolving the weighed polyurethane in an organic solvent, and then adding the metal complex to react, and curing to obtain the shape memory material with the chelating system.

* * * * *